(12) United States Patent
Nikanorov

(10) Patent No.: US 8,322,238 B2
(45) Date of Patent: Dec. 4, 2012

(54) SYSTEM, APPARATUS, AND METHODS FOR EVALUATING MEDICAL DEVICE PERFORMANCE

(75) Inventor: Alexander Nikanorov, Palo Alto, CA (US)

(73) Assignee: Abbott Laboratories, Abbott Park, IL (US)

( * ) Notice: Subject to any disclaimer, the term of this patent is extended or adjusted under 35 U.S.C. 154(b) by 745 days.

(21) Appl. No.: 12/436,725

(22) Filed: May 6, 2009

(65) Prior Publication Data

US 2009/0301182 A1  Dec. 10, 2009

Related U.S. Application Data

(60) Provisional application No. 61/050,930, filed on May 6, 2008, provisional application No. 61/126,755, filed on May 6, 2008, provisional application No. 61/051,001, filed on May 6, 2008, provisional application No. 61/121,482, filed on Dec. 10, 2008.

(51) Int. Cl.
*A61F 2/00* (2006.01)
*G01N 3/00* (2006.01)

(52) U.S. Cl. .................................... 73/866.4; 73/118.01

(58) Field of Classification Search .................. 73/1.82, 73/1.86, 118.01, 865.9, 866.4; 378/4, 207; 434/272

See application file for complete search history.

(56) References Cited

U.S. PATENT DOCUMENTS

| | | | |
|---|---|---|---|
| 6,585,664 B2 * | 7/2003 | Burdorff et al. | 600/564 |
| 6,685,481 B2 * | 2/2004 | Chamberlain | 434/272 |
| 2006/0184005 A1 * | 8/2006 | Sakezles | 600/416 |
| 2008/0006081 A1 * | 1/2008 | Weldon et al. | 73/53.01 |
| 2008/0032273 A1 * | 2/2008 | Macnamara et al. | 434/262 |
| 2008/0076101 A1 * | 3/2008 | Hyde et al. | 434/272 |
| 2008/0109070 A1 * | 5/2008 | Wagner et al. | 623/1.41 |
| 2008/0227073 A1 * | 9/2008 | Bardsley et al. | 434/267 |
| 2011/0288406 A1 * | 11/2011 | Sosna et al. | 378/207 X |
| 2012/0202180 A1 * | 8/2012 | Stock et al. | 434/272 |

FOREIGN PATENT DOCUMENTS

| | | | | |
|---|---|---|---|---|
| DE | 3526813 C1 * | 1/1987 | | 73/865.9 |
| JP | 2006189525 A * | 7/2006 | | |

* cited by examiner

*Primary Examiner* — Thomas P Noland
(74) *Attorney, Agent, or Firm* — Workman Nydegger; Ron Devore

(57) ABSTRACT

Systems, apparatuses, and methods for evaluating medical device performance are provided. A corresponding method may include deploying an implantable medical device into an apparatus for evaluating performance of an implantable medical device. The apparatus may include a support structure and simulated tissue operatively associated with the support structure. The method may further include manipulating the support structure and/or the simulated tissue to simulate physiological forces on the implantable device.

18 Claims, 6 Drawing Sheets

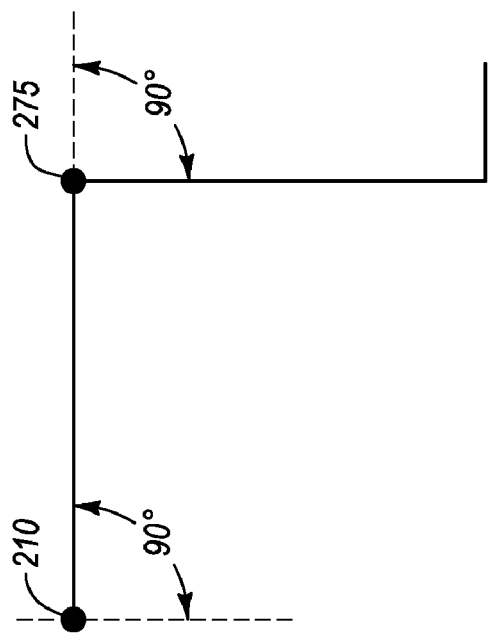
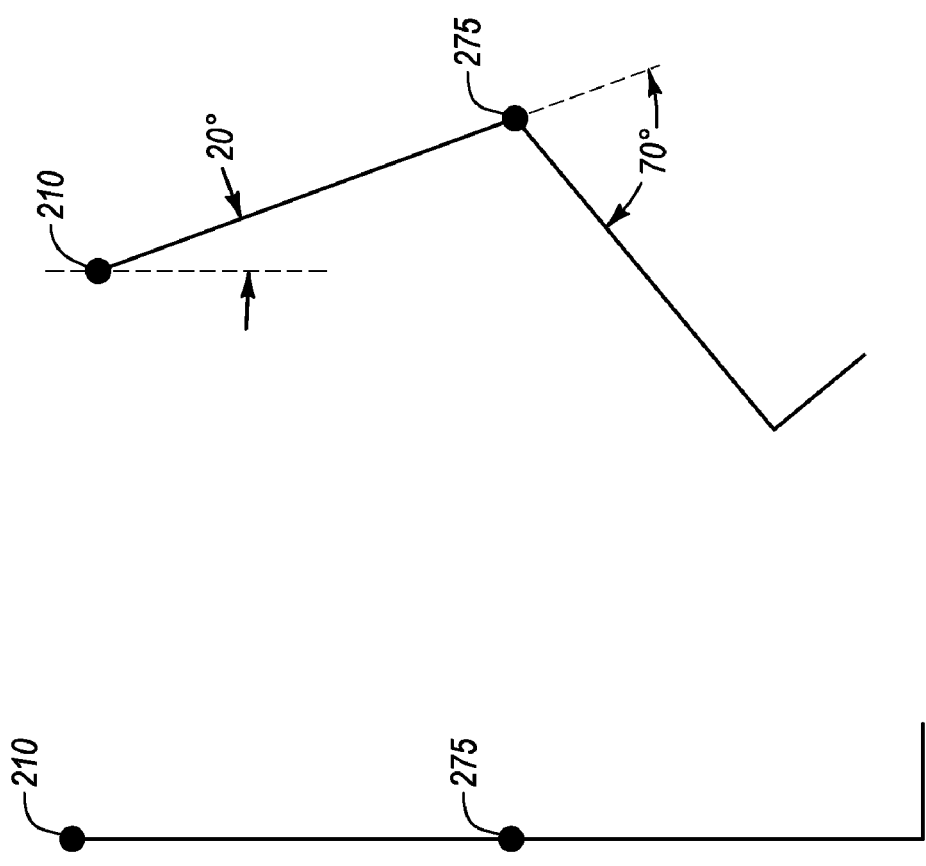
Fig. 4C
Fig. 4B
Fig. 4A

SYSTEM, APPARATUS, AND METHODS FOR EVALUATING MEDICAL DEVICE PERFORMANCE

CROSS-REFERENCE TO RELATED APPLICATIONS

This application claims the benefit of and priority to U.S. Provisional Patent Application No. 61/050,930, entitled "Methods for Imaging an Implantable Device During Use", and filed May 6, 2008, U.S. Provisional Patent Application No. 61/051,001, entitled "Methods for Imaging an Implantable Device During Use", and filed May 6, 2008, U.S. Provisional Patent Application No. 61/126,755, entitled "Methods for Imaging an Implantable Device During Use", and filed May 6, 2008, and U.S. Provisional Patent Application No. 61/121,482 filed Dec. 10, 2008 and entitled "Methods for Imaging an Implantable Imaging Device During Use," each of which is incorporated by reference in its entirety.

BACKGROUND OF THE DISCLOSURE

1. The Field of the Disclosure

The present disclosure relates generally to testing and evaluation of medical devices and, in particular, to testing and evaluation of medical devices while the devices are subjected to dynamic forces.

2. The Relevant Technology

Implantable medical devices can be used to treat conditions interior to a patient, such as within a patient's vascular system. Stents are one type of implantable medical device. Stents are tubular structures generally constructed of metals such as stainless steel, CoCr, Nitinol or other alloys, as well as polymers. Stents can be constructed to be either self-expanding structures that utilize superelastic properties of the material of which they are constructed or balloon-expandable structures that are expanded through plastic deformation. Such devices can be used to treat vascular conditions.

As stenting has become increasingly applied, procedural technical success rates have increased and the superiority of stenting over simple percutaneous angioplasty has been demonstrated. However, occlusive atherosclerotic lesions (blockages) in the femoropopliteal artery can be difficult to treat endovascularly. In particular, in-stent restenosis generally remains a significant clinical problem, as study findings show restenosis in about 46% of stented patients after two years. Restenosis refers to the obstruction of the blood vessel due to the formation of scar tissue in a vessel in response to an adverse interaction between the stent and the vessel wall.

The reasons for the high rate of restenosis in stented femoropopliteal arteries have not been fully elucidated. One hypothesis is that in-stent restenosis may be a function of the unique biomechanical forces (axial extension and contraction, flexion or bending, radial compression, and torsion) present in stented leg arteries. Additionally, stent fractures have been reported, which may be one cause of restenosis. Other studies have detailed attempts to evaluate femoropopliteal motion in vivo and in cadaveric models. These studies, while valuable, are generally expensive to conduct and limited in sample size and scope. These studies have not previously been extended to physiological bench-top model evaluations where numerous samples can be evaluated without difficulty.

Further, while in vivo and cadaveric studies can be useful in providing information about the performance of a single type of medical device in a single realistic environment, it can be difficult to determine performance characteristics of the medical device compared to other medical devices. For example, it could be unduly intrusive or even harmful to introduce various medical devices into a patient for the purposes of evaluating relative performance. Even if such a procedure were undertaken, the environment differences existing within the same patient could vary enough to make useful comparison difficult.

Furthermore, studies involving humans have data varying over a spectrum that does not allow for the accurate portrayal of detecting stent deformations. Clinical and cadaveric studies have expensive procedures in purchasing cadavers, catheter lab equipment, and vendors and may require a skilled physician for handling. Moreover, those studies may be time consuming in acquiring data. Furthermore, clinical and cadaveric studies do not allow for easy observation of the inner-workings of the human leg.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF THE DISCLOSURE

One example implementation of the present disclosure includes a method of testing an implantable medical device. The example method may comprise deploying the implantable medical device in an apparatus for evaluating performance of an implantable medical device. The apparatus may comprise a support structure and simulated tissue operatively associated with the support structure. The method may further comprise manipulating the support structure and/or the simulated tissue of the apparatus to simulate physiological forces on the implantable device. In some implementations, the simulated tissue may include a simulated body lumen and the support structure may include a skeletal support structure. In further implementations, the simulated tissue may include at least one muscular support.

An additional example implementation of the present disclosure may include an apparatus for evaluating performance of an implantable medical device. The apparatus may comprise a support structure and simulated tissue operatively associated with the support structure. The support structure may be formed from a template taken from a human subject and the support structure and simulated tissue may be configured to cooperate to exert dynamic forces on an implantable medical device similar to physiological forces. In some implementations, the support structure may include at least one skeletal support structure, such as a hip, femur, tibia, and/or fibula. In further implementations, the simulated tissue may include at least one muscular support and at least on simulated body lumen.

A yet further implementation of the present disclosure may include a system for evaluating performance of an implantable medical device. The system may include a platform, a skeletal structure operatively associated with the platform, a simulated muscular support operatively associated with the skeletal structure, and a simulated body lumen operatively associated with at least one of the skeletal structure and the muscular support. The system may be configured in such a manner that movement of the skeletal structure simulates physiological forces on an implantable medical device deployed in the simulated body lumen. In some implementations, the system may further comprise a guide channel defined in the platform and a follower assembly coupled to the skeletal structure and operatively associated with the guide channel in such a manner as to constrain movement of the skeletal structure relative to the platform.

Additional features and advantages of the disclosure will be set forth in the description, which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description of the disclosure will be rendered by reference to specific embodiments thereof, which are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which:

FIG. 4 illustrates a chart of physiological motions in accordance with one example of the present disclosure.

Figure 1:
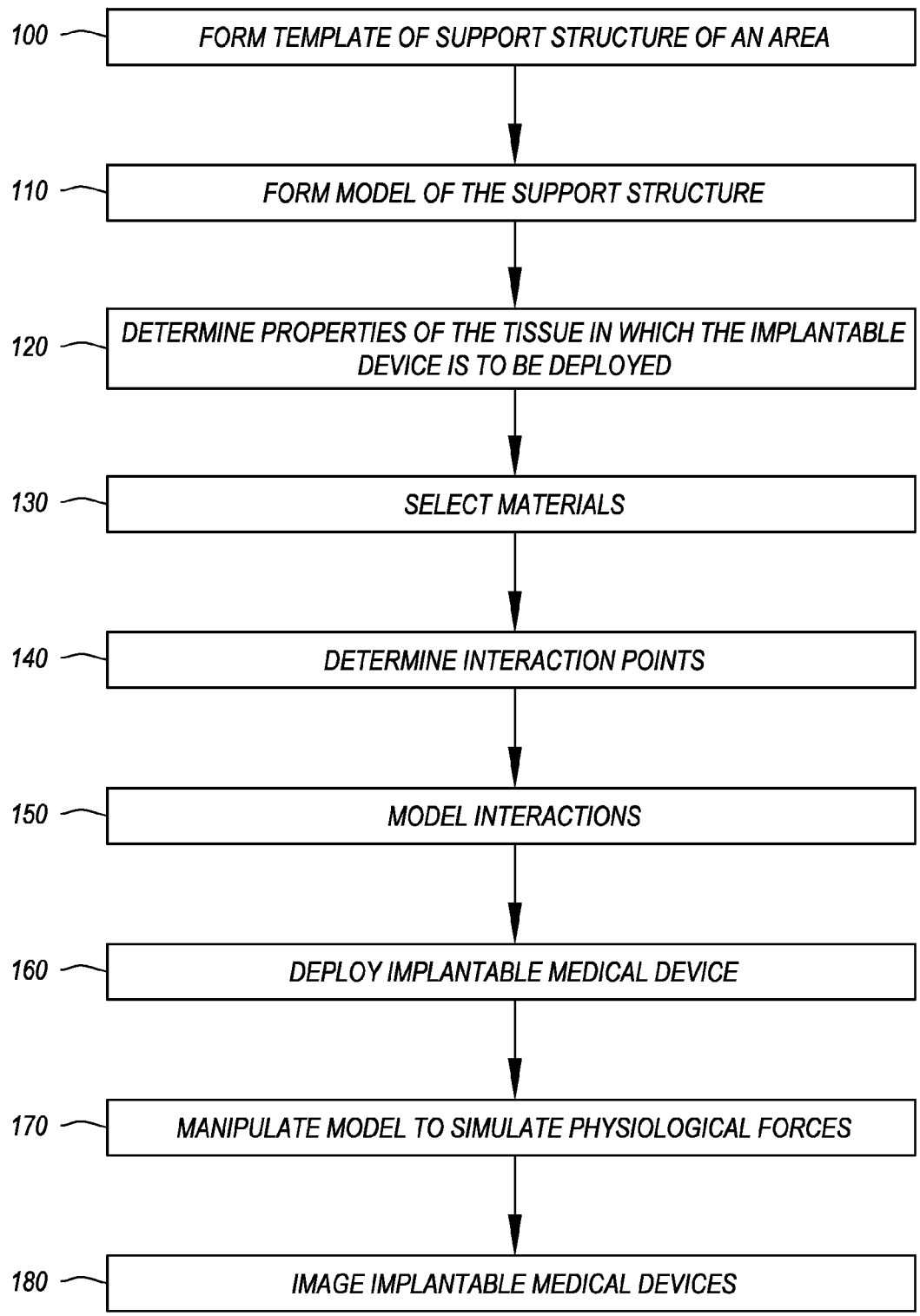
FIG. 1 illustrates a method of evaluating the performance of an implantable medical device according to one example.

Together with the following description, the Figures demonstrate and explain the principles of a system for evaluating medical device performance and methods for using the system for evaluating medical device performance. In the Figures, the thickness, relative position, size, and/or configuration of components may be exaggerated for clarity. The same reference numerals in different Figures may represent similar, though not necessarily identical, components.

DETAILED DESCRIPTION

Systems, apparatuses and methods are provided herein for evaluating the performance of implantable medical devices, such as stents. In at least one example, an apparatus or model is provided that includes structural supports that simulate a base structure of the area in which an implantable medical device is to be deployed. One such model may include skeletal supports, which may be coupled together to provide simulated articulation and dynamic movement as desired. The model may further include material which simulates the tissue in which an implantable medical device is to be deployed. Such material may include simulated vessels and muscular support. Medical devices may be implanted at various locations within the vessels. The models may then be moved or otherwise manipulated to simulate physiological movements and apply corresponding dynamic forces on an implanted medical device. These forces may approximate in vivo physiological forces without invasive procedures. Further, the same forces may be consistently applied to various implantable medical devices.

The use of such a model may serve to reduce inconsistency due to individual anatomical differences with cadaveric models and clinical subjects. Moreover, the model may be highly cost-efficient, may create a controlled environment for variable (tubing length, material, diameter, and thickness) modification, and may allow large sample sizes. Consistently applying forces that simulate the combination of physiological forces present within a human body may allow different implantable medical devices as well as different types or designs of implantable medical devices to be tested in a controlled, consistent manner. Testing implantable medical devices in a controlled, consistent manner may in turn provide meaningful results that may then be used in evaluating the design, including strengths and weaknesses, of implantable medical devices. Further, the medical device may be imaged as the apparatus and/or system is moved or otherwise manipulated. Imaging the implantable medical device while dynamic forces are consistently applied may provide useful information about the potentially complicated movement of the medical device in response to these forces.

The apparatuses, systems, and methods are described below in the context of an implantable stent. It will be appreciated that this configuration is provided for ease of reference only and that apparatuses, systems, and methods may be configured to model physiological forces on any implantable devices for any part of a living system.

FIG. 1 illustrates a flowchart illustrating exemplary methods for evaluating and/or analyzing the performance of an implantable medical device. As will be discussed in more detail below, the method may include the development of a model of an area of the body in which an implantable medical device may be deployed. Accordingly, as illustrated in FIG. 1, the method may include forming a template of the support structure of the area in which a medical device may be implanted, as represented by block 100. A template may be taken from any suitable source. For ease of reference, the template will be discussed as a skeletal template. In one example, the skeletal template may be taken from direct molding of a skeletal structure of a cadaveric model.

In other examples, the skeletal template may be generated using three-dimensional models. Three-dimensional models may be acquired through computerized tomography (CT), X-ray images, and/or any other source. In at least one example, the template may correspond to a human leg. In other examples, the template may correspond to other skeletal structures, such as a neck. In still other examples, the template may correspond to organs or muscle groups.

The method may also include forming a support structure using the template, as represented by block 110. In the case of a skeletal template, one or more skeletal support members may be formed using the template. For example, a skeletal support structure of one or more of the bones may be formed through molding, machining, or other processes of suitable materials to provide sufficient support to simulate the support provided by the skeletal support structure.

With an accurate model of the support structure, development of the model may continue with determining properties for the tissue in which the implantable medical device is to be deployed, as represented by block 120. For example, in the case of a stent, determining the model properties for the tissue in which the implantable medical device is to be deployed may include determining properties of a body lumen, such as a vessel or artery. Such a vessel may include, without limitation, a femoral artery. Such a process may include determining material properties such as Young's modulus, wall strength and penetrability, or any other material properties of a body lumen using any suitable techniques.

Determining properties of the tissue in which the implantable medical device is to be deployed may further include determining properties of muscle surrounding or supporting the body lumen. Similar or different techniques may be used to determine the properties of the muscle as those used to determine the properties of the body lumen. Further, while the support structure and the tissue in which implantable medical devices are to be deployed are discussed separately, it will be appreciated that in at least one example the tissue in which the implantable medical device is to be deployed and the support structure may be the same structure.

Once the properties of the tissue have been determined, materials may then be selected to model the properties, as represented by block 130. The material or materials may be referred to as simulated tissue. Any number of materials may be selected to simulate any number of properties of the tissue in which the implantable medical device is to be deployed.

Simulated vasculature may be formed as described in U.S. patent application Ser. No. 11/748,374, entitled "Forming Vascular Diseases within Anatomical Models", and filed May 14, 2007, which is herein incorporated by reference in its entirety. For example, anatomical models may be provided with simulated plaque, a lesion, a chronic total occlusion, other vascular diseases, or combinations thereof. Forming of vascular diseases in the model may create a variety of testing models.

The vascular disease may be formed separately from the structured anatomical model. The formed vascular disease material may be bonded to or within a PVA, silicone, or other material in a separate process from forming this simulated vascular disease, thus providing a replicated specific anatomy structure with an abnormality for demonstrating, testing, and/or developing medical functions and/or devices.

In embodiments using PVA, the bonding of the lesion material may be done during the forming of the anatomical model itself (i.e., while injecting liquid PVA into a mold), or in a separate process from molding the anatomical model. For example, the vascular disease may be attached to a preformed piece of PVA using a process for bonding of two pieces of PVA material—e.g., where the lesion and/or PVA material can be coated with liquid PVA solution and adjoined next to the usually partially processed piece of PVA and a curing cycle can be performed thereon.

The above process may be combined with other embodiments described herein and in various manners to also provide for more complex anatomical models. For example, one or more of specific models formed from pre-molded pieces of partially processed PVA may be joined using a bonding process described below. Further, the lesion or other vascular disease may also be added to the preformed, partially processed portion of PVA or other material before, during, or after bonding. Of course, other combination of process are also recognized and contemplated herein.

After the materials have been selected and/or processed, the method may include determining the interaction points between the support structure and the tissue, as represented by block 140. For example, a body lumen may interact with a skeletal support at a number of locations as well as the surrounding muscles at a number of locations. Any number of interaction points may be determined. Further, any number of interaction points may be omitted as desired for modeling purposes. This step may further include determining the type of interaction to be modeled at each of the interaction points. Types of interaction may include a fixed interaction, a semi-fixed interaction, viscous translation with respect to a point, and/or any other type of interaction.

Thereafter, the interaction between the fixing points or other model materials may be modeled, such as through the use of fixed supports, semi-fixed supports, loosening of the interaction between the support structure and the muscular supports, and/or lubrication of channels, etc., as represented by block 150. At this point, the model may be ready to apply dynamic forces to an implantable medical device.

Accordingly, as represented by block 160 an implantable medical device may be deployed at a desired location within the model. Thereafter, the model may be manipulated to apply dynamic forces to simulate physiological forces as represented by block 170. For example, the skeletal structure may be manipulated and/or dynamic forces applied to the muscular supports to simulate physiological forces. These forces may be generated cyclically or in any manner desired. In at least one example, these forces may be repeated cyclically until an implantable medical device fails. Such a process may provide useful information about the fatigue life of implantable medical devices. Further, such a process may also provide useful information as to the failure mode of implantable medical devices as well as the location of the failure. The results may also be performed in a controlled manner so as to provide repeatability between devices to thereby provide a relatively large sample size with statistically significant results. In at least one example, manipulating the model may include establishing relative movement between skeletal components. In other examples, manipulating the model may include applying an external force to simulated musculature to simulate muscular contraction and extension. In other examples, manipulating the model may include applying forces to simulate organ function.

In addition to providing useful information as to failure of implantable medical devices, the application of dynamic forces in such a setting may allow for the ready imaging of implantable medical devices, as represented by block 180. Imaging medical devices during the application of dynamic forces which simulate physiological forces may provide useful information as to how such forces combine to act on the implantable medical device, including providing information as to axial extension and contraction, flexion or bending, radial compression, and/or torsion that acts on implantable medical devices when deployed. In at least one example, a model may be developed for evaluating the performance of an implantable medical device, such as a stent, within a femoral artery. One example of a model of a femoral artery will now be discussed in more detail with reference to FIGS. 2A-2C.

Figure 2A:
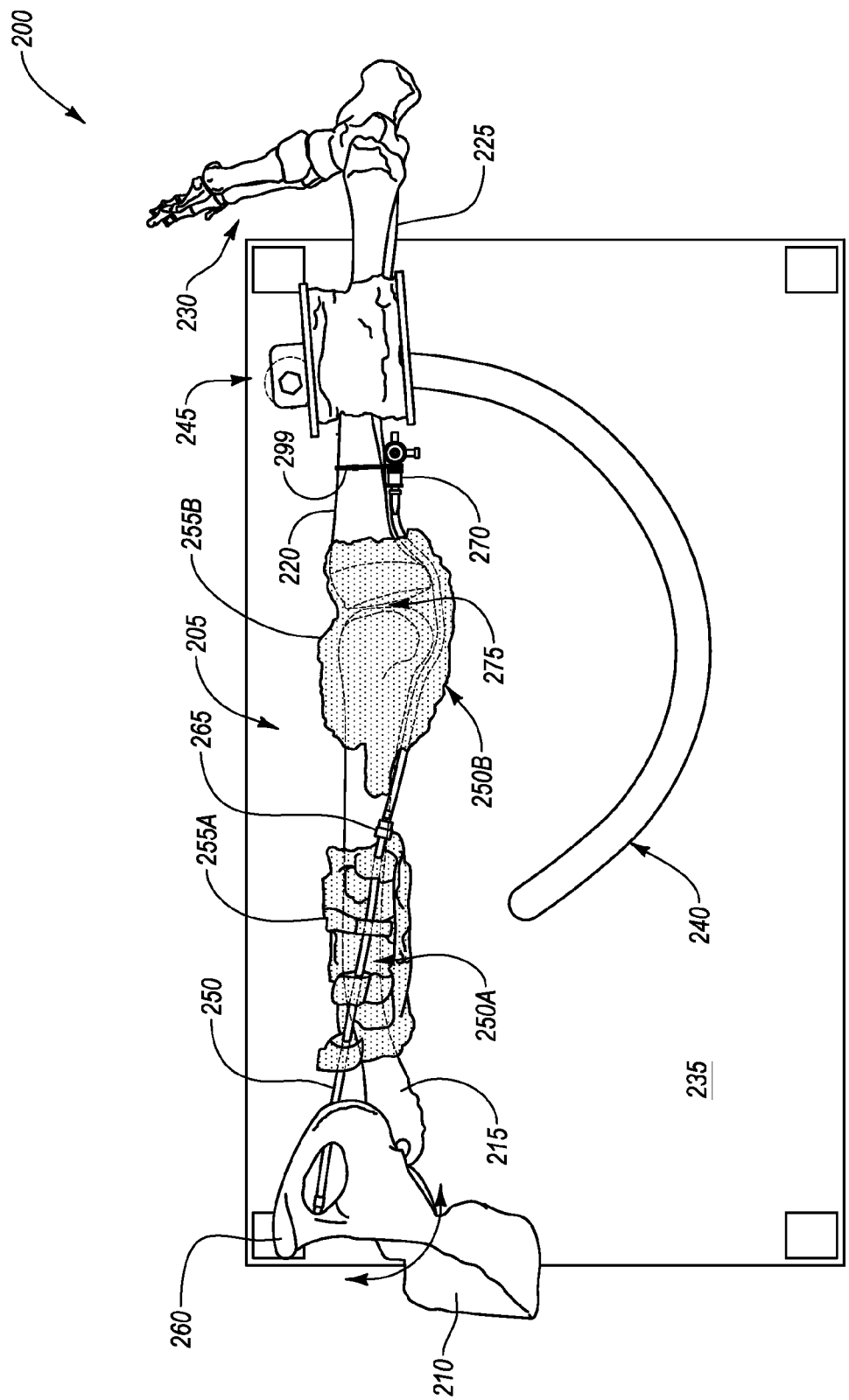
FIG. 2A illustrates a system for evaluating the performance of an implantable medical device in a first state according to one example.

FIG. 2A illustrates a system 200 for modeling physiological forces acting on an implantable medical device. For ease of reference, the anatomical names of the components of the system 200 are used and described both in vivo conditions as well as those replicated in the system 200. In the illustrated example, the system 200 includes an apparatus or model of a human leg having a skeletal structure 205 that includes a hip 210, a femur 215, a tibia 220, a fibula 225, and a foot structure 230. In the illustrated example, the skeletal structure 205 is supported by a platform 235. In particular, the hip 210 may be secured to the platform 235 to allow relative rotation of the hip 210 relative to the platform 235 and relative rotation of the femur 215 relative to the hip 210. In at least one example, the platform 235 may be generally planar. Further, the platform 235 may generally be oriented to simulate a sagittal plane.

The femur 215 may be operatively associated with the tibia/fibula 220/225 in such a manner as to allow relative rotation there between. In the illustrated example, a guide channel 240 may be defined in the platform 235. A follower assembly 245 may be operatively associated with the tibia 220 and/or the fibula 225 and the guide channel 240 in such a manner that movement of the tibia/fibula 220/225 may be constrained to a path that is generally parallel to the platform 235. As previously introduced, the hip 210 may be secured to the platform 235. The fixing of the hip 210 to the platform 235 and the constraint of the movement of the tibia 220 and the fibula 225 to a path parallel to the platform 235 may thereby constrain movement of the skeletal structure 200 to movements that are parallel to the sagittal plane and that simulate human leg physiological motions.

Any suitable material may be used in forming the bones of the skeletal structure 205. In at least one example, pre-fabricated poly-vinyl chloride axial skeletal bones (hip, femur, tibia, fibula, and foot) may be affixed onto the platform 235 as shown. The skeletal structure 200 may support any number of body lumens, such as a simulated femoral artery 250.

In vivo, various interactions between a femoral artery, musculature, and bones may contribute to physiological forces acting on a deployed implantable medical device within the femoral artery. This interaction may be modeled between the simulated femoral artery 250, skeletal structure 200, and muscular supports, shown modeled as muscular supports 255A, 255B. In at least one example, these interaction points may be modeled by routing the simulated femoral artery 250 through a femoral bifurcation 260, through an adductor canal defined in the muscular support 255A to an adductor hiatus 265 and through muscular support 255B to the location of an anterior tibial artery branch 270. In the illustrated example, securing structures 299, such as, barbed fittings, zip ties, and zip-tie holders may be placed at the two main fixed points of the skeletal structure 205 at the femoral bifurcation 260 and the anterior tibial artery branch 270. Such a configuration may help the system 200 generate dynamic forces similar to physiological forces present with in vivo or cadaveric models. The simulated femoral artery 250, the muscular supports 255A, 255B, and any other structures may be prepared of any desired materials.

In at least one example, the simulated femoral artery 250 may have material properties, such as an elastic modulus, that are in the same order of magnitude as that of human femoral arteries. For example, the simulated femoral artery 250 may be formed from silicone tubing of 0.75 mm thickness and 5 mm internal diameter (Young's modulus 2.2±0.3 MPa). In other examples, simulated body lumens may be provided that have material properties that may have a different order of magnitude than a corresponding body lumen. For example, in some implementations, the Young's modulus may range from 0 to 4 MPa.

Fluid may be disposed through the simulated femoral artery to simulate blood flow. For example, in one embodiment, water can be continuously perfused through the simulated femoral artery at a temperature of about 37° C. and at a rate of about 270 ml/min. In further embodiments, the fluid used, the temperature of the fluid, and/or the rate of perfusion may vary to achieve a desired simulation. For example, in some embodiments, the temperature of the fluid may range from 34° C. to 40° C. and the flow rate may range from 100 ml/min to 500 ml/min.

The elastic modulus of human femoral arteries is reported in the literature to be approximately 1.5 MPa, in the radial direction. In at least one example, vascular graft material and/or silicon tubing may be selected as the body lumen material. In other examples, other poly-vinyl alcohol (PVA), or other synthetic polymers or combination thereof may be used. Further, natural body lumens, such as porcine arteries, may also be used as desired. The following illustration displays the stress-strain curves of various tubing materials:

Any suitable material or materials may also be chosen for the muscular supports 255A, 255B. The muscular supports 255A, 255B may be formed of the same material or different materials as desired. Suitable materials may include, without limitation, polymeric materials, or thermoplastic elastomers, such as Dermasol or other elastomers. The muscular supports 255A, 255B may be secured to the skeletal structure 200 as desired, such as by molding the material directly onto the skeletal structure 200 and then cutting some portion of the material away from the skeletal structure as desired to simulate interaction between an in vivo skeletal structure and in vivo musculature. Further, the material may then have a lubricant applied thereto, such as synthetic oil lubricants and/or other similar lubricants. Such a configuration may allow muscular support 255A to simulate adductor musculature and muscular support 255B to simulate muscular support around the knee joint. This simulated muscular support in turn may help the system 200 to simulate physiological forces exerted on the simulated femoral artery 250 and, in particular, on a superficial femoral artery (SFA) 250A and on a popliteal artery (PA) 250B.

In vivo, the SFA begins distal to the bifurcation of the common femoral artery separating the SFA and a deep femoral portion may be modeled by fixing the simulated femoral artery 250 adjacent the femoral bifurcation 260.

In vivo, the SFA runs through the adductor canal until it reaches the adductor hiatus, where it becomes the popliteal artery (PA). The SFA is contained within an adductor canal, which is a space formed by the large muscles of the leg. When the muscles that form the adductor canal contract, their diameter may be enlarged, transmitting transversal tension to the wall of the vessel. This tension causes the blood vessel to glide longitudinally in relation to the canal wall. This is known as the gliding mechanism of the SFA. Since the SFA lies between the hip and knee joints, hip and knee flexion will act upon the SFA. However, it is reported that the walls of the adductor canal are not involved in knee flexion, suggesting the vessel inside the adductor canal only slides longitudinally during these movements. For the elderly, this gliding mechanism within the walls of the adductor canal may be impaired due to an accumulation of tissue around the arteries, called perivascular fibrosis. In addition, this sliding mechanism impairment may be due to the natural elongation of the artery and the loss of the arterial elasticity through age.

In at least one example, muscular support 255A may simulate the adductor canal muscles that may be formed using oiled highly elastic Dermasol material (California Medical Innovations, Pomona, Calif.). Dermasol may be molded to the skeletal structure 200 and then cut away to allow for some movement relative to the skeletal structure 200. The simulated femoral artery 250 may then be threaded through holes in the muscular support 255A. Since the simulated femoral artery 250 may be supported by the muscular support 255A and may slide freely, muscular support 255A may not impart significant active forces on the simulated femoral artery 250 during movement of the system 200. Accordingly, the muscular support 255A may help limit side movements of the SFA 250A while allowing the SFA 250A to slide longitudinally, which is an accurate portrayal of the gliding mechanism.

The platform 235 generally allows for movement of the hip 210 and tibia/fibula 220/225 skeleton about the hip 210 and knee joint 275 in the sagittal plane as described above. The hip joint in the sagittal plane allows flex from about 0° to about 90° as shown. A normal knee joint typically involves a rolling and sliding motion. In vivo, the femur, tibia/fibula, and the two cruciate ligaments form a four-bar linkage that dominates the anteroposterior movement during knee flexion. Thus, an imaginary point may be established on the femur 215 and the tibia/fibula 220/225 may be rotated around that point while corresponding measurements are taken. For every about 30° of flexion from about 0° to about 90°, the distance between the point and the tibia may be reduced by about 0.25 inches. This may be taken into account when creating the platform 235 and the corresponding guide channel 240. Accordingly, the system 200 may generally simulate the leg movements in the physiological positions.

In vivo, the PA runs behind the knee from the adductor hiatus to the origin of the anterior tibial artery. The artery is fixed at the adductor hiatus (proximal) and the origin of the anterior tibial artery (distal). The muscle enclosing the lower and middle PA is the gastrocnemius muscle. In the illustrated example, the gastrocnemius muscle may be simulated as muscular support 255B, which may be formed as a passive Dermasol support molded to the knee joint with ample space for simulated arterial motion. Accordingly, the system 200 may be configured to simulate an in vivo structure. The structure may then be manipulated as desired to simulate physiological forces acting on an implantable medical device.

Figure 2B:
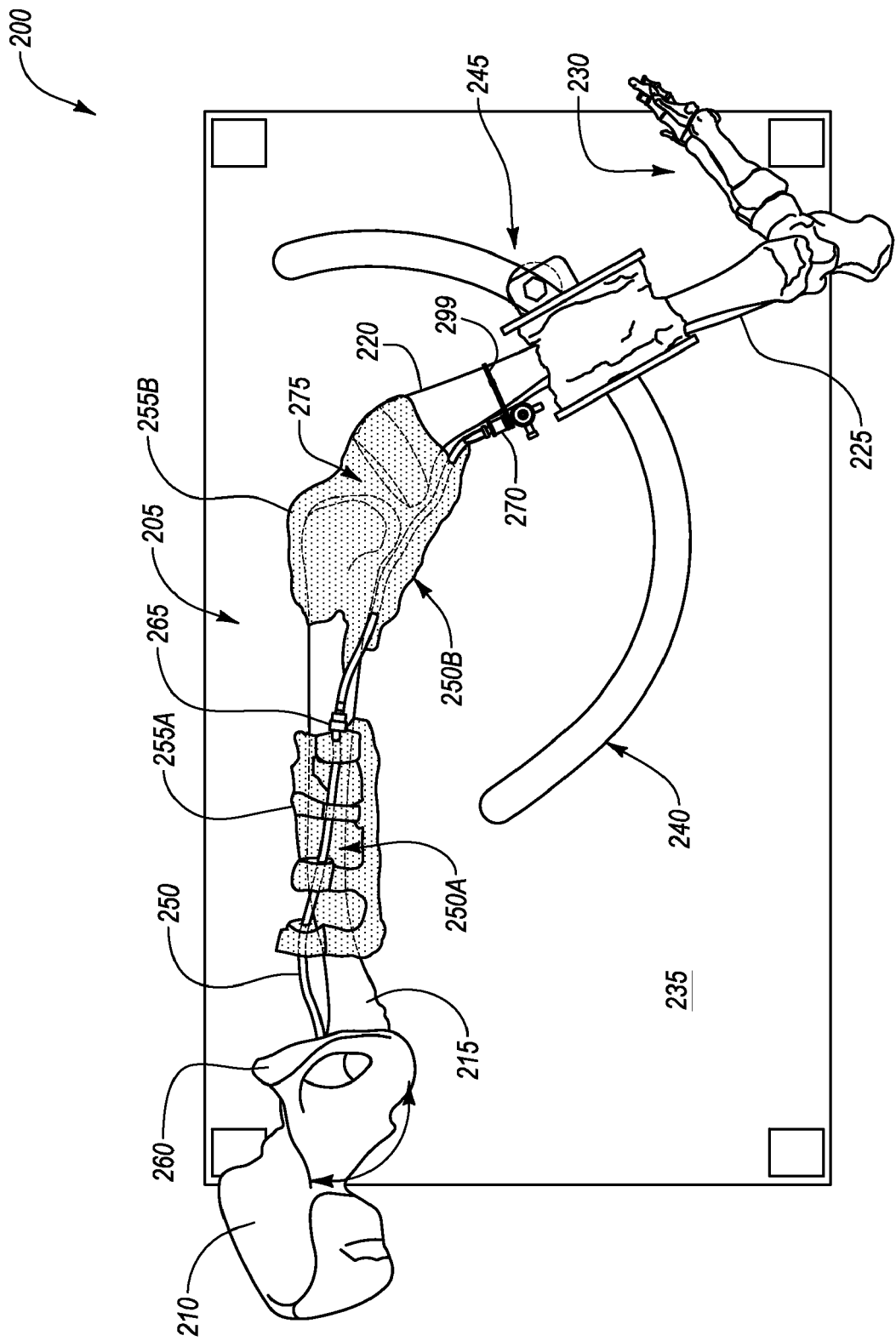
FIG. 2B illustrates a system for evaluating the performance of an implantable medical device in a second state according to one example.
Figure 2C:
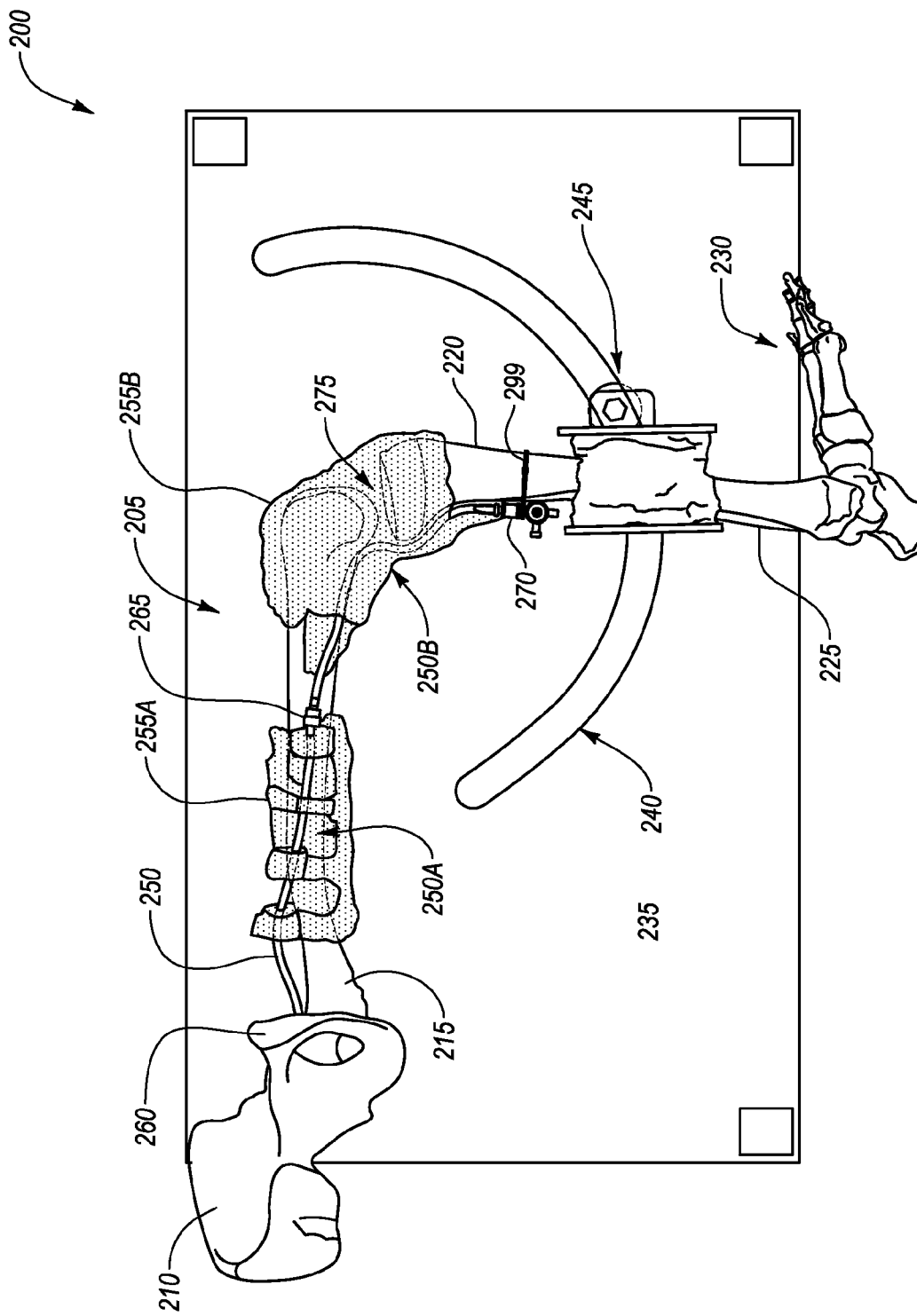
FIG. 2C illustrates a system for evaluating the performance of an implantable medical device in a third state according to one example.

FIGS. 2A-2C illustrate the system 200 moving between various states to simulate compression/extension under three physiological motions: straight-leg (no knee or hip flexion, FIG. 2A), walking (flexion in knee of 70° and flexion in hip of 20°, FIG. 2B) and sitting or stair climbing (flexion in knee of 90° and flexion in hip of 90°, FIG. 2C).

These configurations may be used to provide conditions for the evaluation of an implantable medical device. Radiograph images may then be obtained at the respective physiological motions shown in FIGS. 2A-2C. In particular, radiopaque rulers may be placed on the same plane as the simulated femoral artery 250 for image analysis. Contrast agent may be injected into the simulated femoral artery 250. Still fluoroscopic images may then be taken of the native simulated femoral artery 250 before stent implantation with the hip/knee angle at about 0/0, about 20/70, and about 90/90 degrees as shown in FIGS. 2A-2C.

Thereafter, a representative stent may be deployed at the target location within simulated femoral artery 250 in the straight leg position shown in FIG. 2A. Any type of implantable medical device may be used, including those used in cadaveric models. Such a process may facilitate direct comparison with existing cadaveric model data. Still fluoroscopic images may be taken of the stented region with the hip/knee angle at about 0/0, about 20/70, and about 90/90 degrees as shown in FIGS. 2A-2C. The images may then be analyzed, such as through the use of software. For example, the images may be analyzed using Sigmascan Pro software to determine changes in length and bending of the stented artery. Accordingly, the implantable medical device may then have dynamic forces applied thereto as desired to provide information about the performance of the implantable medical device.

In a further implementation, the materials used for the simulated femoral artery 250 and muscular supports 255A, 255B may be at least partially transparent. Accordingly, the performance of the stent may be visually observed by a technician without the aid of imaging devices.

While one template and system is described, it will be appreciated that any model used may be labeled as representative of the population because studies involving live or cadaveric subjects will have many anatomical variations. Studies involving humans have data varying over a spectrum that does not allow for the accurate portrayal of detecting stent deformations. Next, models are advantageous because the environmental variables of the body lumen are controlled. For example, the tubing elasticity, thickness, inner diameter, and outer diameter are controlled. In cadaveric and clinical studies, the arterial elasticity and wall vary depending on age and anatomy. The model may also be used with unlimited sample size. Repetitive tests may be performed to obtain more statistically significant data. Additionally, the model may be inexpensive to fabricate and easy to operate. Furthermore, the model may facilitate observation of the inner-workings of the simulated human leg, especially where the stent is placed. In addition, the model may serve to gauge the range of possible outcomes and compare the relative impact to previous studies.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

EXAMPLE 1

The purposes of this example study included 1) developing a representative in-vitro model of the Femoropopliteal Artery (FPA) that simulates physiological hip and knee motion and 2) using the model to characterize the types and ranges of stent distortion produced by extremity movement.

A comparative axial elasticity evaluation was conducted between the tubing intended to simulate arteries and ex-vivo porcine carotid arteries. The model was assessed for its native (unstented) and stented arterial bending and axial compression/extension under various physiological motions.

The model demonstrated stent bending and compression generally as previously observed in cadaver studies. Proximity of results between model and cadaver studies indicate that results obtained from the model studies may be representative of results that would be achieved from cadaver studies. As a result, this example may allow a better understanding of vascular device performance in the dynamic FPA and improvement on future stent designs.

This example study included two portions: 1) Model development and 2) Model testing. Model development included addressing the following areas: the skeleton, muscle support and arterial fixation, artery simulation, and model assembly.

Skeleton—The pre-fabricated bones for the skeletal structure were composed of Polyvinyl Chloride and included the hip, femur, tibia, fibula, and foot (Pro-Med Products, Alpharetta, Ga.). The bones were fabricated from a mold of a 5'6" male. The leg skeleton was deconstructed by the hip joint and knee joint and restructured according to measured angles. The femur was fixed onto an acrylic platform. The platform generally allowed for movement of the hip and tibia/fibula skeleton by the hip joint and knee joint in the sagittal plane, respectively. In particular, the hip joint was restricted as a hinge joint on the acrylic platform. Thus, it was able to flex from about 0° to about 90° as marked on the acrylic platform. The realistic alignment and rotational movement of these components were considered in model development. The model generally simulates the leg movements in the physiological positions labeled in FIG. 4.

When considering skeletal motions, the hip joint was generally restricted to a hinge joint in the sagittal plane. Although a normal hip joint involves a ball and socket, freely rotating in many dimensions, this restriction was introduced to simulate motions in existing cadaver studies for comparison. This allowed measurements to be taken with the model at angles the same as those used in the cadaver study.

Muscle Support and Arterial Fixation—The superficial femoral artery (SFA) begins distal to the bifurcation of the common femoral artery separating the SFA and deep femoral. The artery is tethered at this bifurcation, so this was modeled as a fixed arterial attachment point. The SFA runs through the adductor canal until it reaches the adductor hiatus, where it becomes the popliteal artery (PA).

The adductor canal muscles were modeled using oiled highly elastic Dermasol material (California Medical Innovations, Pomona, Calif.). Dermasol was molded to the simulated skeleton and then cut away to allow for some arterial movement within the material. A simulated artery was threaded through holes in the Dermasol. The simulated artery was supported by the Dermasol and could slide freely, but the Dermasol did not impart any active forces on the artery during hip and knee bending.

As discussed above, the SFA ends and the PA begin at the adductor hiatus. The adductor hiatus is at the end of the adductor canal where the upside-down "V" of the adductor magnus muscle encloses the artery. This landmark involves compression by the adductor magnus on the artery during knee flexion. As a result, this region was modeled as a semi-fixed point. In particular, the simulated artery was enclosed in Dermasol at the adductor hiatus but the Dermasol at this point was not oiled, thereby disabling free sliding of the simulated artery. In the model, the gastrocnemius muscle was simulated as a passive Dermasol support molded to the knee joint with ample space for simulated arterial motion.

The Dermasol muscle support restricted side movements of the tubing but allowed it to slide longitudinally, which was an accurate portrayal of the gliding mechanism discussed in more detail herein. The placement of Dermasol and artery tubing were justified by recreating 3D objects using 2D images from lateral and anterior positions found in VisibleBody.com (accessed Jun. 30, 2008).

Artery Simulation—No known available tubing is able to simulate the exact properties of a human vessel. To find the closest match for clinical relevance, several materials were assessed and examined for their material properties in comparison with ex-vivo porcine carotid arteries (Pel Freeze Biologicals, Rogers, Ark.). The investigated materials included Dermasol, Silicone, a vascular graft, and Polyvinyl Alcohol (PVA).

The Dermasol DS-302 is from a family of thermoplastic elastomers compounded by California Medical Innovations (Pomona, Calif.). Raw material was made into about a 5 mm inner diameter and about a 2-3 mm wall thickness tubing through a dip-molding process. Silicone tubing was Dow Corning Q7-4750 5.0 mm ID×0.75 mm wall thickness, supplied by Specialty Silicone Fabricators (Paso Robles, Calif.). PVA tubing was fabricated with raw material from Fisher Scientific (Pittsburgh, Pa.). Gelweave vascular grafts were manufactured by Vascutek (Scotland, UK). Two comparative studies were conducted with the tubing: 1) An investigation into stent tubing interaction and recoil and 2) An axial elasticity evaluation.

The investigation into stent-tubing interaction and recoil evaluated only Dermasol and Silicone tubing. Two cable tie mounts, 20 mm by 20 mm, were placed 200 mm apart. The tubing was cut out to fit both barb fittings on each side and included tubing stretched 85% of its original 200 mm gap length. For example, 170 mm of tubing spanned the 200 mm gap and additional tubing was used to fit the barb fittings. Once the tubing was in place, the stent was deployed in the tubing. Self-Expanding Absolute® Nitinol Stents with radiopaque markers (Abbott Vascular, Santa Clara, Calif.) were deployed using a delivery system. Upon deployment, the stent length was measured. The tubing was marked to indicate both ends at the barb fitting and at the ends of the stents, including the radiopaque markers. The tubing was then removed from the cable ties and gently placed at a relaxed position next to a ruler. The stent length and contracted tubing length was measured. The stent was then removed from the tubing by cutting a slit through the tubing. The tubing was then measured again for validation of full contraction.

In Dermasol tubing, the stent compressed about 2.0% and the tubing compressed about 8.8% when released from the barb fittings. In Silicone tubing, the stent compressed about 5.1% and the tubing compressed about 11.2%. Stents had approximately the same initial deployed length inside each type of stretched tubing. When the tubing was placed at a relaxed position, there was a significant difference in length between both tubing. The Silicone tubing typically has more axial rigidity and was able to contract the stent when the tubing was placed in the rest position. Dermasol was more elastic and did not force the stent to contract. Additionally, the tubing with the indications at the respective four points showed decreased stent length in the unstretched tubing. Upon removal of the silicone tubing from the mounts, the stent slid axially outward relative to the tubing. The stent did not do this with the Dermasol tubing.

Figure 3:
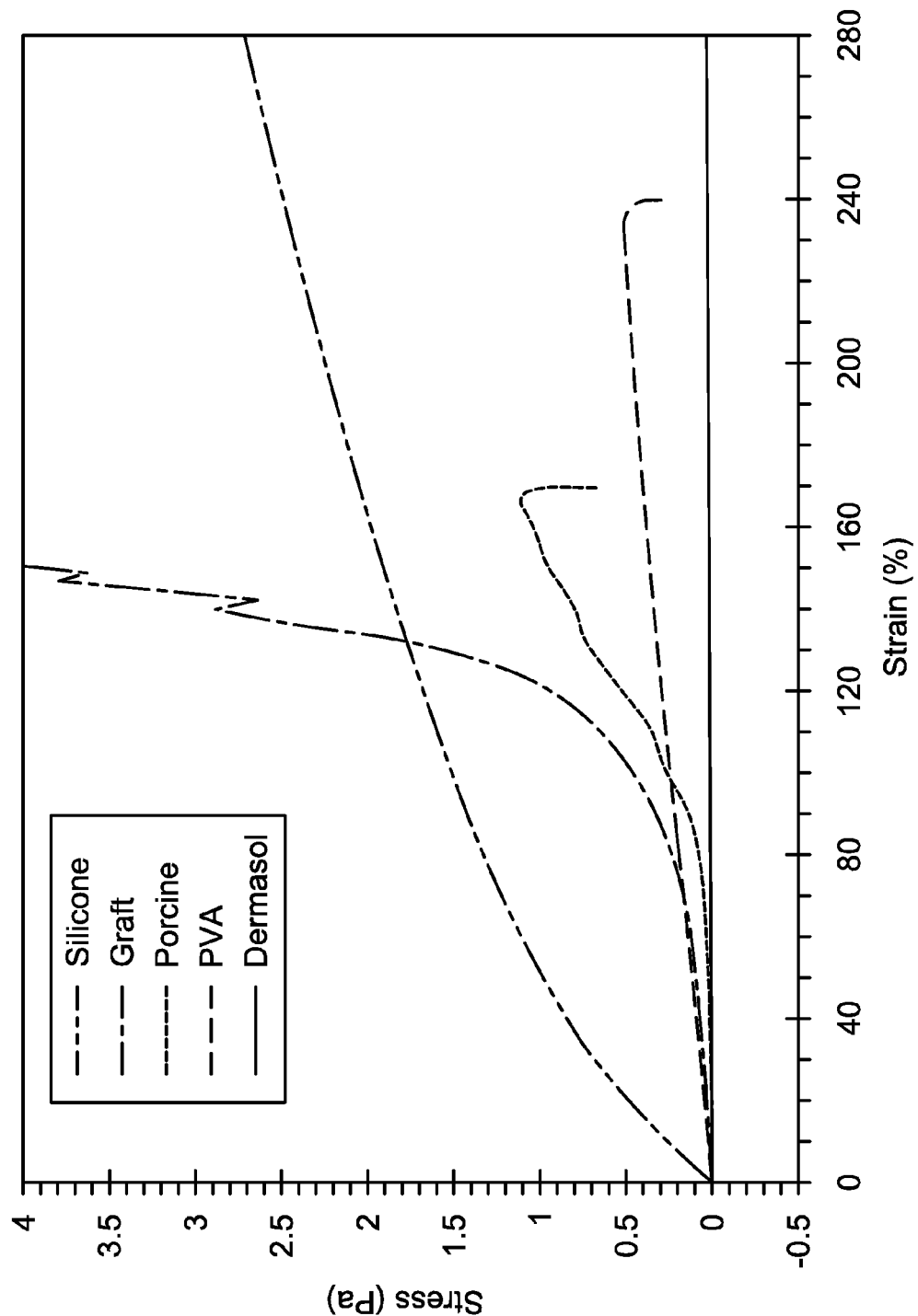
FIG. 3 illustrates a stress strain curve in accordance with the present disclosure.

The axial elasticity investigation evaluated Dermasol, Silicone, Gelweave vascular graft, and ex-vivo porcine carotid arteries, pulled using an Instron tensile tester (Model 5565/C5677, ±500 N load cell, rate of 10 in/min) (n=5). Cylindrical samples of each sample were obtained and cut to 5 mm each. The carotid arteries had generally inconsistent inner and outer diameters and white, elastic collagen surrounding the vessel. All cylindrical samples were longitudinally slit open using scissors that were flattened for the test. The samples were placed between the clamps of the Instron and sand paper was used on the grips for the artery and graft runs to prevent slippage during testing. Results of the testing were interpreted using the stress-strain analysis shown in FIG. 3. The resulting Young's Moduli are shown in the following table:

| | Silicone | Vascular Graft | Porcine Carotid Artery | PVA | Dermasol |
|---|---|---|---|---|---|
| Young's Modulus (MPa) | 2.2 ± 0.3 | 0.26 ± .05 | 0.07 ± 0.02 | 0.25 ± 0.03 | 0.0067 ± 0.0031 |

Young's modulus is defined by the slope of the linear section of the stress versus strain curve for a particular material. Stress was calculated by dividing the force (output by the Instron) by the cross-sectional area of the sample. Strain was calculated by dividing the change in length (Instron travel) by the initial set length for each sample. Silicone tubing was chosen to represent the arteries in the model.

Model Assembly—Holes were drilled on the leg skeleton to attach to the acrylic platform. Barbed fittings, zip ties, and zip-tie holders were placed at the two main fixed points of the leg skeleton. Dermasol was used to simulate the muscle elasticity. Dermasol was cast on the skeleton with foil and tubing was placed in the region where the simulated tubing would take place. The tubing used to cure the knee area had an outer diameter of about 14 mm, while the simulated silicone vessel had an outer diameter of about 6.5 mm.

Next, the model was subject to a variety of tests. First, the silicone tubing was stretched about 14% of its original length and placed in the barbed model fittings. A previous cadaver study noted the distal SFA shortened about 23% while the PA shortened about 14%. The model typically can use only one measurement for shortening because the simulated vessel is one continuous piece of tubing. Most observed bending takes place in the PA, and therefore about 14% was used as an appropriate shortening measurement of the entire region.

Warm water (about 37±5° C.) was pumped via machine (Cole-Parmer Instrument Company, pumped at about 270 mL/min at tubing size 24) through the silicone simulated vessel tubing. Radiograph images were obtained at the respective physiological motions using a GE GEC 9800. Radiopaque rulers were placed on the same plane as the artery for image analysis. Contrast agent was injected into the simulated artery and still fluoroscopic images were taken of the native simulated model before stent implantation with the hip/knee angle at about 0/0, about 20/70, and about 90/90 degrees.

Then, a 6 mm×100 mm Absolute® stent was deployed at the target location within silicone tubing in the straight leg position. Absolute® stents were used to facilitate direct comparison with existing cadaveric model data. Still fluoroscopic images were taken of the stented region with the hip/knee angle at about 0/0, about 20/70, and about 90/90 degrees. Images were analyzed using Sigmascan Pro software to determine change in length and bending of the stented artery. The measurement process was generally identical to that used in the previous cadaveric model study.

The stent shortening (axial compression) results are shown in the following table:

| Angle | Bench Model (n = 3) | | Cadaveric Model (n = 4) | |
|---|---|---|---|---|
| | 0/0 to 20/70 | 0/0 to 90/90 | 0/0 to 20/70 | 0/0 to 90/90 |
| Mid-SFA | 4.5 ± 0.3 | 8.4 ± 0.7 | 3 ± 2 | 3 ± 3 |
| PA | 7.0 ± 0.3 | 8.0 ± 0.2 | 6 ± 4 | 11 ± 5 |

The bending results are shown in the following table:

| Angle | Bench Model (n = 3) | | Cadaveric Model (n = 4) | |
|---|---|---|---|---|
| | 0/0 to 20/70 | 0/0 to 90/90 | 0/0 to 20/70 | 0/0 to 90/90 |
| Mid-SFA | 1.7 ± 0.6 | 3.3 ± 0.6 | 3 ± 4 | 4 ± 3 |
| PA | 40 ± 5 | 74 ± 3 | 33 ± 21 | 54 ± 25 |

For reference, previously reported cadaveric data is shown next to the model data in the above tables. As shown, stent shortening, interpreted as axial compression, is generally greater in the PA as compared to the Mid-SFA in the about 20/70 hip/knee angle configuration in both the bench model and the cadaveric model. In the about 90/90 hip/knee angle configuration, the model demonstrates similar stent shortening in the PA and Mid-SFA due to uniform silicone tubing in the model. The model appears to yield results in stent bending and compression that are similar to the cadaveric model study. In the PA, bending at about 0/0 hip/knee angle was in the opposite direction of bending at about 20/70 and about 90/90. At about 0/0, the angle of the artery was not 180°; rather, it ranged from about 193° to about 196°. Reported values in the table above are the change in bending angle from about 0/0 to about 20/70 and from about 0/0 to about 90/90.

In artery tubing evaluations, the porcine carotid artery may have properties similar to the human FPA of the materials tested. In some evaluations the human FPA and the porcine carotid artery may be very similar. The elastic modulus of human femoral arteries used for comparison may be approximately 1.5 MPa, in the radial direction. The artery tubing may be designed to have a similar elastic modulus. At least some silicone tubing may have an axial elastic moduli within the same order of magnitude as a typical human femoral artery circumferential elastic modulus. The silicone tubing may provide clarity and/or improved results with respect to general stent-tubing interactions and/or recoil evaluations.

Models may be designed using at least one similarity to cadaveric data. Attributes of the various embodiments of a model may include a generally reasonable structure, similarities in relationships with respect to a typical human body, other attributes, or combinations thereof may result in a model that may be representative of actual stent performance. Embodiments of the models described herein may be developed using reasonable assumptions such as spatial orientations of the anatomy to the joint, arterial, and/or muscular movements of the human body, other assumptions, or combinations thereof. Anatomy may play a role in the development of a model and may be considered during fabrication of the model. Aspects of models may involve creating corresponding assumptions to facilitate usability of an embodiment of the model. Measurement and/or positioning procedures may be identified in a previous cadaveric study and compared with those used in embodiments of a model.

The model may simulate movements of the FPA, the hip, and the knee. Accuracy of the movements may be compared to a cadaveric study. Assumptions used in various embodiments of the models described herein may be justified by literature review.

What is claimed is:

1. A method of testing an implantable medical device, comprising:
    deploying the implantable medical device in an apparatus for evaluating performance of an implantable medical device, the apparatus comprising:
        a support structure; and
        simulated tissue operatively associated with the support structure; and
    manipulating the support structure and/or the simulated tissue to simulate physiological forces on the implantable device.

2. The method of claim 1, wherein the simulated tissue includes at least one simulated body lumen.

3. The method of claim 1, wherein the support structure includes at least one skeletal support structure.

4. The method of claim 3, wherein the at least one skeletal support structure includes a plurality of leg bones.

5. The method of claim 4, wherein the simulated tissue further includes at least one muscular support.

6. The method of claim 5, wherein the simulated tissue includes a simulated femoral artery passing through the muscular support.

7. The method of claim 6, wherein the muscular support comprises a thermoplastic elastomer.

8. The method of claim 6, wherein the simulated femoral artery includes a simulated superficial femoral artery.

9. The method of claim 6, wherein the simulated femoral artery includes a simulated popliteal artery.

10. The method of claim 5, wherein manipulating the support structure and/or the simulated tissue to simulate physiological forces on the implantable device includes providing relative movement between at least two of the leg bones.

11. The method of claim 1, further comprising imaging the implantable medical device.

12. The method of claim 11, wherein imaging the implantable medical device includes taking a computer tomography scan and/or an X-Ray.

13. The method of claim 1, further comprising determining the deflection angle, axial compression, torsion, localized bending, and/or radial compression of the implantable medical device.

14. The method of claim 1, further comprising cyclically manipulating the support structure and/or simulated tissue to simulate cyclical physiological forces on the implantable device until failure of the implantable device.

15. A system for evaluating performance of an implantable medical device, comprising:
 a platform;
 a guide channel defined in the platform;
 a skeletal structure operatively associated with the platform;
 a follower assembly coupled to the skeletal structure, the follower assembly being operatively associated with the guide channel in such a manner as to constrain movement of the skeletal structure relative to the platform;
 a simulated muscular support operatively associated with the skeletal structure; and
 a simulated body lumen operatively associated with at least one of the skeletal structure and the muscular support in such a manner that movement of the skeletal structure simulates physiological forces on an implantable medical device deployed in the simulated body lumen.

16. The system of claim 15, wherein the skeletal structure simulates a leg and wherein interaction between the follower assembly and the guide channel constrains movement of the skeletal structure in a sagittal plane.

17. The system of claim 16, wherein simulated muscular support includes a thermoplastic elastomer and the simulated body lumen includes silicone tubing.

18. The system of claim 17, wherein the skeletal structure includes a hip, femur, tibia, and fibula.

* * * * *